(12) United States Patent
Ubaidulla et al.

(10) Patent No.: US 10,064,875 B2
(45) Date of Patent: Sep. 4, 2018

(54) TOPICAL FORMULATIONS COMPRISING A STEROID

(71) Applicant: Dr. Reddy's Laboratories Ltd., Hyderabad, Telangana (IN)

(72) Inventors: Udhumansha Ubaidulla, Namakkal (IN); Sateesh Kandavilli, Plainsboro, NJ (US); Ajay Sunil Vairale, Hyderabad (IN); Jeffrey A. Wayne, Markham (CA); Vijendra Nalamothu, Basking Ridge, NJ (US); Mistry Meghal, Ahmedabad (IN); Refika Isil Pakunlu, Highland Park, NJ (US)

(73) Assignee: PROMIUS PHARMA LLC, Princeton, NJ (US)

( * ) Notice: Subject to any disclaimer, the term of this patent is extended or adjusted under 35 U.S.C. 154(b) by 0 days.

(21) Appl. No.: 15/928,332

(22) Filed: Mar. 22, 2018

(65) Prior Publication Data

US 2018/0207178 A1   Jul. 26, 2018

Related U.S. Application Data

(63) Continuation of application No. 15/843,590, filed on Dec. 15, 2017, now Pat. No. 9,956,231, which is a continuation of application No. 15/690,851, filed on Aug. 30, 2017, now Pat. No. 9,877,974, which is a continuation of application No. 15/495,148, filed on Apr. 24, 2017, now Pat. No. 9,775,851, which is a continuation of application No. 15/226,684, filed on Aug. 2, 2016, now Pat. No. 9,655,907, which is a continuation of application No. 15/135,298, filed on Apr. 21, 2016, now Pat. No. 9,439,911, and a continuation of application No. 15/135,259, filed on Apr. 21, 2016, now Pat. No. 9,433,630, and a continuation of application No. 13/391,972, filed on May 7, 2012, now Pat. No. 9,364,485, and a continuation of application No. 13/391,972, filed as application No. PCT/US2010/047240 on Aug. 31, 2010, now Pat. No. 9,364,485.

(60) Provisional application No. 61/256,554, filed on Oct. 30, 2009.

(30) Foreign Application Priority Data

Aug. 31, 2009 (IN) ............... 2111/CHE/2009

(51) Int. Cl.
*A61K 8/02* (2006.01)
*A61K 31/573* (2006.01)
*B05B 11/00* (2006.01)
*B05B 1/30* (2006.01)
*B05B 1/02* (2006.01)
*A61K 31/58* (2006.01)
*A61K 47/38* (2006.01)
*A61K 47/14* (2017.01)
*A61K 47/44* (2017.01)
*A61K 47/10* (2017.01)
*A61K 9/00* (2006.01)
*A61K 47/36* (2006.01)
*B05B 15/30* (2018.01)

(52) U.S. Cl.
CPC .......... *A61K 31/573* (2013.01); *A61K 9/0014* (2013.01); *A61K 31/58* (2013.01); *A61K 47/10* (2013.01); *A61K 47/14* (2013.01); *A61K 47/36* (2013.01); *A61K 47/38* (2013.01); *A61K 47/44* (2013.01); *B05B 1/02* (2013.01); *B05B 1/30* (2013.01); *B05B 11/3045* (2013.01); *B05B 15/30* (2018.02)

(58) Field of Classification Search
CPC ........ A61K 8/4953; A61K 8/498; A61K 8/64; A61K 9/501; A61K 2800/413; A61K 31/196; A61K 31/24; A61K 31/27; A61K 31/28; A61K 31/426; A61K 31/444; A61K 31/5377; A61K 31/5517; A61K 31/555; A61K 31/566; A61Q 3/00; A61Q 7/00; A61Q 17/04; A61Q 19/004; A61Q 19/007; A61Q 1/00; A61Q 1/02; A61Q 5/006; A61Q 5/02

See application file for complete search history.

(56) References Cited

U.S. PATENT DOCUMENTS 6,075,056 A * 6/2000 Quigley, Jr. ............ A61K 31/57
514/649

* cited by examiner

*Primary Examiner* — Nannette Holloman
(74) *Attorney, Agent, or Firm* — Stites & Harbison, PLLC; Mandy Wilson Decker; Sean P. Ritchie

(57) ABSTRACT

The application provides formulations for the topical administration of an active agent comprising at least one steroid, in the form of topical sprays that are propellant-free, and/or substantially non-foaming, and/or alcohol-free. The present application also provides processes for preparing such compositions and methods of using them in management of skin diseases or disorders such as psoriasis, dermatoses, and other associated skin diseases or disorders.

17 Claims, 3 Drawing Sheets

TOPICAL FORMULATIONS COMPRISING A STEROID

RELATED APPLICATIONS

This application is a continuation of U.S. patent application Ser. No. 15/843,590, now allowed, which claims priority to which claims priority to U.S. Pat. Nos. 9,877,974, 9,775,851, 9,655,907, 9,433,630, 9,439,911, and 9,364,485, which claim priority to International Patent Application No. PCT/US2010/047240 filed Aug. 31, 2010, which claims priority to U.S. Provisional Patent Application No. 61/256,554 filed Oct. 30, 2009 and Indian Patent Application No. 2111/CHE/2009 filed Aug. 31, 2009, the entire disclosures of each of which are incorporated herein by this reference.

INTRODUCTION

Aspects of the present application provide pharmaceutical topical sprayable compositions comprising at least one steroid as an active agent. The present application also provides compositions that are useful in the prophylaxis, amelioration or treatment of skin diseases or disorders, such as psoriasis, steroid responsive dermatoses, and associated diseases or disorders. The present application further provides processes for preparing the compositions and methods of administration of the compositions onto the skin, in the form of sprays.

Psoriasis, a chronic, idiopathic, genetically determined, and environmentally influenced disorder has been treated empirically for centuries with varied success. Its association with arthropathy and its significant psychological consequences have necessitated a comprehensive team approach for optimal care. Psoriasis is a non-contagious autoimmune disease which affects the skin and joints. It commonly causes red scaly patches to appear on the skin. The scaly patches caused by psoriasis, called psoriatic plaques, are areas of inflammation and excessive skin production. Skin rapidly accumulates at these sites and takes on a silvery-white appearance. Plaques frequently occur on the skin of the elbows and knees, but can affect any area including the scalp and genitals. In contrast to eczema, psoriasis is more likely to be found on the extensor aspect of the joint. The disorder is a chronic recurring condition which varies in severity from minor localized patches to complete body coverage. Fingernails and toenails are frequently affected (psoriatic nail dystrophy) and can be seen as an isolated finding. Psoriasis can also cause inflammation of the joints, which is known as psoriatic arthritis. Ten to fifteen percent of people with psoriasis have psoriatic arthritis. The cause of psoriasis is not known, but it is believed to have a genetic component. There are many treatments available, but because of its chronic recurrent nature psoriasis is a challenge to treat.

At present, corticosteroids are being increasingly used in the therapy of psoriasis. The corticosteroids are a class of compounds comprising steroids (lipids that contain a hydrogenated cyclopentoperhydrophenanthrene ring system) elaborated by the adrenal cortex (except sex hormones of adrenal origin) in response to the release of adrenocorticotrophin or adrenocorticotropic hormone by the pituitary gland, or to any synthetic equivalent, or to angiotensin II. In pharmacologic doses, corticosteroids are used primarily for their anti-inflammatory and/or immunosuppressive effects.

Various other therapies are also being used in treatment of psoriasis. Keratolytic agents, applied topically, provide adjunctive aid in helping to control stable hyperkeratotic forms of psoriasis. Ointment and creams containing coal tar, dithranol (anthralin), vitamin $D_3$ analogues (for example, calcipotriol), and retinoids are routinely used. Some of the systemic chemotherapeutic options have been used to help control severe forms of psoriasis. The three main traditional systemic treatments are methotrexate, cyclosporine and retinoids. Methotrexate and cyclosporine are immunosuppressant drugs; retinoids are synthetic forms of vitamin A. Other drugs, found to be effective in psoriasis, include the antimetabolite tioguanine, the cytotoxic agent hydroxyurea, sulfasalazine, the immunosupressants mycophenolate mofetil, azathioprine and oral tacrolimus. In 2008, three new treatment options were approved in the U.S. for treating psoriasis: 1) Taclonex® Scalp, a topical ointment for treating scalp psoriasis; 2) the Xtrac® Velocity excimer laser system, which emits a high-intensity beam of ultraviolet light and can treat moderate to severe psoriasis; and 3) the biologic drug adalimumab (brand name Humira®) for treating moderate to severe psoriasis.

Topical corticosteroids, such as betamethasone dipropionate, are effective in treatment of corticosteroid-responsive dermatoses primarily because of their anti-inflammatory, antipruritic and vasoconstrictive actions. Betamethasone dipropionate is an analog of prednisolone, and has a high degree of corticosteroid activity and a slight degree of mineralocorticoid activity. Betamethasone dipropionate is of particular value when used in short courses for the treatment of more resistant dermatoses such as psoriasis (excluding widespread plaque psoriasis), atopic dermatitis, and other skin conditions that do not respond satisfactorily to less active steroids.

The drug compound having the adopted name "betamethasone dipropionate" has a chemical name 9-fluoro-11(β),17,21-trihydroxy-16(β)-methylpregna-1,4-diene-3,20-dione 17,21-dipropionate and is represented by structural Formula I.

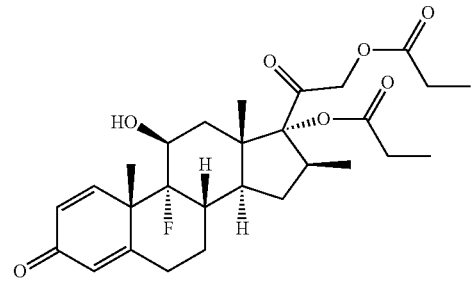

Formula I

Betamethasone dipropionate is a white to cream white, crystalline powder. It is practically insoluble in water, sparingly soluble in ethanol and freely soluble in acetone and chloroform.

Topical betamethasone dosage forms, such as aerosol foam, cream, ointment, gel, and lotion formulations are commercially available. Combination formulations of the betamethasone dipropionate with calcipotriene hydrate and also with clotrimazole exist. Betamethasone dipropionate is the active ingredient in commercially available products sold as DIPROLENE AF® and DIPROLENE® that comprise 0.05% betamethasone base, intended for application to affected skin areas once or twice daily.

U.S. Pat. Nos. 6,126,920 and 7,078,058 disclose betamethasone valerate aerosols with a quick-break foaming agent, a propellant, and a buffering agent, wherein ethanol is present. U.S. Pat. No. 5,369,131 discloses a liquid mechanically foamable pharmaceutical composition, which is propellant free, for local application. U.S. Patent Application Publication No. 2008/0102039 discloses spray foaming dosage compositions comprising propylene glycol. U.S. Pat. No. 5,958,379 discloses a pharmaceutical composition that is sprayable as liquid droplets, forming a preparation within times less than 4 seconds. U.S. Patent Application Publication No. 2006/0239929 discloses a sprayable composition for the treatment of psoriasis, comprising clobetasol as the active agent together with ethyl alcohol.

U.S. Patent Application Publication No. 2009/0098069 discloses an alcohol-free composition comprising a physiologically active agent, one or more dermal penetration enhancers, selected from the group consisting of ethers of diethylene glycol and ester sunscreens, and one or more non-volatile liquids in an alcohol-free composition.

U.S. Patent Application Publication No. 2008/0300229 claims a pharmaceutical/dermatological composition comprising a corticoid solubilized in a vehicle comprising an oily phase, comprising one or more oils, with no vitamin D derivative. A corticoid can be clobetasol propionate.

U.S. Patent Application Publication No. 2008/0206155 discloses a non-alcoholic foaming pharmaceutical emulsion composition, comprising an effective amount of a steroid (hydrocortisone, hydrocortisone acetate, desonide, betamethasone valerate, etc.) as an active pharmaceutical agent having a degree of solubility in the emulsion composition, an unctuous emollient, and at least one liquefied or compressed gas propellant, being packaged in an aerosol container.

Corticosteroids in the forms of alcohol solutions, lotions, creams, and ointments are conventionally used for the treatment of skin diseases in humans, such as, for example, eczema, infantile eczema, atopic dermatitis, dermatitis herpetiformis, contact dermatitis, seborrheic dermatitis, neurodermatitis, psoriasis, and intertrigo. Many formulations containing such active substances are greasy, and hence are unpleasant to apply on large areas of the skin. Ineffectiveness of lotion, cream, and ointment formulations is observed, since they are generally too viscous to allow efficient penetration of the active agent in the epidermis, and a solution composition has a tendency to evaporate before the active agent penetrates the epidermis. In addition, some conventional cream and ointment bases are irritating to the skin, particularly over the long exposure that is frequently required for efficacy, and the fluidity of lotions often makes the physical application difficult to control over a desired area. Moreover, it is necessary to rub such formulations into the target site to improve the penetration of the active agent into the epidermis, an action which itself produces irritation. The formulations containing ethanol suffer the well known adverse effects of ethanol, i.e., irritation. Further many formulations contain propylene glycol, which is an excellent vehicle and solvent for preparation of dermatologic dosage forms; however, since propylene glycol has a tendency to induce irritant or allergic skin reactions, such formulations do not promote patient compliance. Additionally, pressurized aerosol (propellant based) formulations in the market have the disadvantage of relatively high cost, primarily due to the construction of the containers and metering valves. Also, the propellant based formulations have undesirable environmental impact.

Another disadvantage of conventional formulations is that their active agents act for a short duration of time and thus require frequent re-application, thereby providing a negative impact on treatment compliance and quality of life of the patient. Furthermore, several steroidal formulations are available that cause substantial foam formation upon spraying onto the skin, which is highly undesirable to a patient using such preparations for aesthetic reasons. Several topical formulations available commercially are primarily incapable of providing the much needed soothing effect to the affected areas, particularly in conditions such as psoriasis. The disadvantages of topical agents vary, in that they can often irritate normal skin, be time consuming and awkward to apply, cannot be used for long periods, can stain clothing, and/or have an objectionable odour. As a result, it is sometimes difficult for people to maintain regular applications of these medications. Abrupt withdrawal of some topical agents, particularly corticosteroids, can cause an aggressive recurrence of the condition. This is known as "rebound" of the condition.

There remains, therefore, an unmet need for improved patient compliant topical formulations that are effective in the treatment of skin disorders such as psoriasis, and which provide improved delivery of the active agent at the desired site of action, with decreased inconvenience and irritation, increased ease of use for the patient, and longer duration of action.

SUMMARY

Aspects of the present application provide sprayable pharmaceutical topical compositions comprising at least one steroid as an active agent.

In aspects, the present application provides pharmaceutical topical spray compositions comprising at least one steroid as an active agent and being to propellant-free and/or substantially non-foaming.

Aspects of the present application provide processes for preparing propellant-free topical spray compositions.

Aspects of the present application provide methods of using propellant-free topical spray compositions comprising at least one steroid as an active agent. In embodiments, methods of using comprise administering a pharmaceutically effective amount of a spray composition directly onto an affected part of the skin of a subject in need thereof.

In aspects, the present application provides uses of propellant-free topical spray compositions comprising at least one steroid as an active agent for prophylaxis, amelioration, or treatment of psoriasis, steroid responsive dermatoses, erythema, contact sensitivity reactions, and other associated diseases or disorders.

In embodiments, compositions of the present application are aqueous based emulsion sprays.

Aspects of the application provide propellant-free sprayable topical pharmaceutical compositions, comprising an active agent, an emulsifying agent, a polymer, water, a water-immiscible substance, and an active agent skin penetration enhancer in amounts about 0.001-15 percent by weight.

Aspects of the application provide propellant-free sprayable topical pharmaceutical compositions comprising a betamethasone compound, in amounts equivalent to about 0.025 to about 0.1 percent by weight of betamethasone base, an emulsifying agent, a polymer, water, a water-immiscible substance, and an active agent skin penetration enhancer in amounts about 3 to about 10 percent by weight.

Aspects of the application provide processes for preparing a propellant-free pharmaceutical topical sprayable composition, comprising:

a) heating a mixture comprising an emulsifying agent and a water-immiscible substance to obtain an oily phase;

b) optionally, mixing an antioxidant, preservative, or both with the oily phase of a);

c) mixing an active agent with a penetration enhancer;

d) mixing the material of c) with the mixture of a) or b);

e) dissolving a polymer in water; and f) mixing the oily phase of d) with an aqueous phase of e), to form an emulsion.

DETAILED DESCRIPTION

Figure 1:
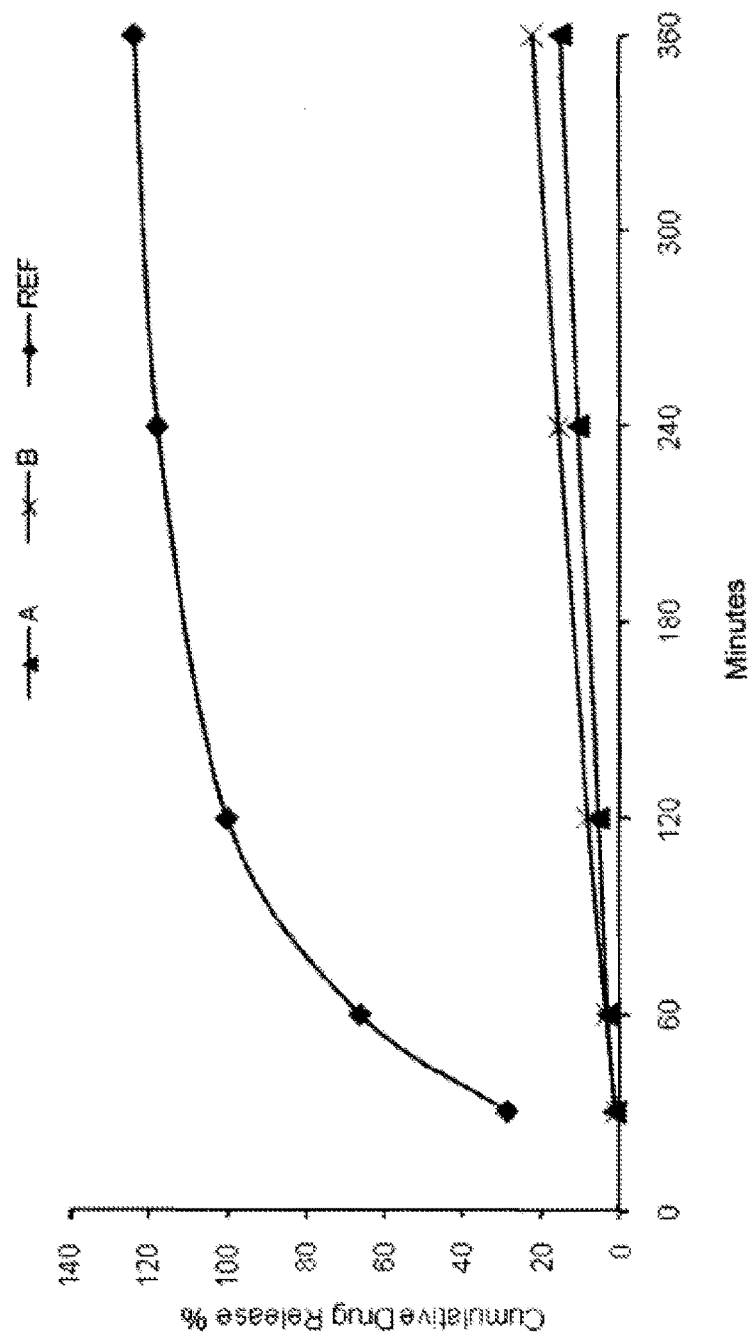
FIG. 1 shows comparative in vitro dissolution profiles of drug released from formulations prepared in Example 1, and a commercially available reference product.

The term "stable" as used herein refers to physical stability and/or chemical stability of the active agent in a topical composition, wherein changes in the drug assay values and/or impurities content are less than about 10%, during stability study storage of the composition at 25° C. and 60% relative humidity (RH), or 30° C. and 65% RH, or 40° C. and 75% RH, for durations such as 3, 6, 12, 18, or 24 months.

The term "propellant free" as used herein indicates that the compositions are not delivered in admixture with any of the commonly used aerosol propellants, such as fluorochlorohydrocarbons, hydrocarbons, compressed gases, and the like.

The term "substantially free" as used herein indicates that a specified substance referred to is present in amounts not more than 10% by weight of the total composition.

Aspects of the present application provide pharmaceutical topical compositions comprising at least one steroid as an active agent, which is non-irritating to the skin, non-toxic, and well-tolerated.

In an aspect, the present application provides pharmaceutical topical spray compositions comprising at least one steroid as an active agent, the compositions being propellant-free and/or substantially non-foaming.

In an aspect, the compositions of the present application are aqueous based emulsion sprays.

In an aspect, a steroid is present in its acid or base form, its salt form, its ester form, its isomer form, or as a prodrug thereof.

In embodiments, a steroid of the present application is betamethasone, or a salt, ester, isomer, derivative, or prodrug thereof.

In embodiments, betamethasone is present in the form of betamethasone dipropionate.

In embodiments, a steroid of the present application is mometasone furoate.

In embodiments, a steroid of the present application is betamethasone valerate.

In embodiments, a steroid of the present application is triamcinolone acetonide.

In embodiments, a steroid of the present application is alclometasone dipropionate.

In an aspect, an active agent can be added in an amorphous form, crystalline form, or mixtures thereof.

In an aspect, a composition of the present application is easily manufactured, non-irritating to the skin, non-toxic, and well-tolerated, thereby providing a high degree of patient compliance, and is useful in the prophylaxis, amelioration or treatment of skin diseases or disorders such as psoriasis, steroid responsive dermatoses, erythema, contact sensitivity reactions, and other associated diseases or disorders.

In an aspect, formulations of the present application provide sustained release of the active agent, for better skin permeation and patient comfort.

In embodiments, compositions of the present application are substantially alcohol-free and/or propylene glycol-free.

In an aspect, compositions of the present application are physically and chemically stable for commercially relevant times.

In an aspect, the present application provides methods of using propellant-free topical spray compositions comprising at least one steroid as an active agent, methods comprising administering a pharmaceutically effective amount of a spray composition directly onto an affected part of the skin of a subject in need thereof.

In an aspect, pharmaceutical topical spray compositions of the present application are useful in the management of psoriasis, and further can provide a moisturizing and/or soothing effect at the site of application to the skin. In an aspect, a composition reduces the dryness that accompanies the build-up of skin in psoriatic plaques. In an aspect, a composition can be applied directly to the psoriatic lesions or dermatoses and can help reduce inflammation, remove built-up scale, reduce skin turnover, and/or clear affected skin of plaques.

In an aspect, the present application provides propellant-free topical compositions in a sprayable form, comprising at least one active agent, at least one solvent, at least one emulsifying agent, at least one polymer, and at least one skin penetration enhancer in an amount of about 0.001 to about 15%, by weight, wherein a composition provides an enhanced flux of the active agent through the localized region of the body surface to reach the dermis layer, thus being useful in the prophylaxis, amelioration, or treatment of skin diseases or disorders.

In embodiments, a penetration enhancer is present in a composition in amounts about 0.05 to about 10%, by weight. In embodiments, a penetration enhancer is present in a composition in amounts about 3% to about 10%, by weight.

In an aspect, the skin diseases or disorders treated using compositions of the application include psoriatic plaques, steroid responsive dermatoses, erythema, contact sensitivity reactions, and other associated diseases or disorders.

In an aspect, the skin diseases or disorders treated using compositions of the application include atopic dermatitis, seborrhoeic dermatitis, eczema, plaque psoriasis, erythrodermic psoriasis, psoriasis of the scalp, and any combinations thereof.

In an aspect, the present application provides methods of prophylaxis, amelioration, or treatment of skin diseases or disorders, comprising administering a pharmaceutically effective amount of a spray composition to a subject in need thereof. In aspects, the skin diseases or disorders are psoriasis, steroid responsive dermatoses, erythema, contact sensitivity reactions, and other associated diseases or disorders.

In embodiments, compositions of the present application comprise one or more additional active agents that are useful in the management of psoriasis and associated pathological conditions including synthetic, semi-synthetic, or naturally obtained active agents.

The compositions of the present application can be used for prophylaxis, amelioration, or treatment of skin diseases and disorders, comprising administering a pharmaceutically effective amount of a spray composition to a subject in need thereof. The compositions of the present application are also useful in conjunction with other therapies, such as phototherapy.

In embodiments, compositions of the present application are easily water-washable and removable from the site of application. In embodiments, compositions of the present application, when applied by spraying onto the skin, are substantially non-occlusive to the skin.

In embodiments, compositions of the present application are substantially alcohol-free and/or propylene glycol-free, such that any amounts present do not cause significant skin irritation or impart any undesired attributes to the composition.

In embodiments, compositions comprise at least one steroid as an active agent and one or more excipients, in the form of topical sprays. Concentrations of an active agent contained in a composition of the present application range from about 0.01% to about 10%, or from about 0.025% to about 0.5%, by weight.

An aspect of the present application provides dispensing devices containing propellant-free topical compositions, wherein a device comprises a container, a pump dispenser, a dip tube, a metering valve, and an actuator, and wherein the pump dispenser is capable of dispensing the composition through a dip tube into a metering valve, and through the actuator fitted with an orifice, such that the composition is consistently released in the form of a substantially uniform spray.

An aspect of the present application provides dispensing devices containing a propellant-free topical composition; wherein the devices comprise a container having therein a pouch system or bag filled with the composition, optionally fitted with a dip tube and an actuator fitted with a valve, the container being filled with a gas such as nitrogen gas or compressed air, surrounding the pouch or bag. Introduction of the composition into the system can further increase the pressure of the system, which is capable of dispensing the composition from the pouch or bag into the actuator fitted with a valve, such that the composition is released upon actuation in the form of a spray.

An aspect of the present application provides processes for preparing propellant-free topical compositions in sprayable form, comprising at least one steroid as an active agent.

In embodiments, advantages of topical sprayable formulations of the present application include one or more of non-irritancy to the site of application, ease of application, usefulness for long periods, non-staining of fabrics, and not possessing a strong or objectionable odour. This facilitates a subject in need thereof to maintain regular applications of the medications, thus avoiding abrupt withdrawal of the steroidal composition applications, which in turn prevents an aggressive recurrence of the disease condition.

In embodiments, compositions of the application comprise at least one steroid drug, such as alclometasone dipropionate, amcinonide, beclomethasone dipropionate, betamethasone benzoate, betamethasone dipropionate, betamethasone sodium phosphate, betamethasone valerate, budesonide, clobetasol propionate, clobetasone butyrate, clocortolone pivalate, desonide, desoximetasone, dexamethasone, dexamethasone acetate, dexamethasone nicotinate, dexamethasone propionate, dexamethasone sodium phosphate, dexamethasone valerate, diflorasone diacetate, diflucortolone valerate, fluandrenolide, flumethasone pivalate, fluocinolone acetonide, fluocinonide, fluocortin butyl ester, fluticasone propionate, halcinonide, halobetasol propionate, halometasone monohydrate, hydrocortisone, hydrocortisone sodium phosphate, hydrocortisone sodium succinate, hydrocortisone-17-butyrate-21-propionate, hydrocortisone aceponate, hydrocortisone acetate, hydrcortisone valerate, hydrocortisone butyrate, hydrocortisone probutate, methylprednisolone, methylprednisolone acetate, methylprednisolone aceponate, mometasone furoate, prednisolone, prednisolone sodium phosphate, prednisolone acetate, prednisolone-17-valerate-21-acetate, triamcinolone acetonide, triamcinolone acetate, triamcinolone diacetate, and prednicarbate. Other drug compounds are also useful, and this application further specifically contemplates the use of any combinations of steroid drugs.

According to the invention, unless otherwise specified, recitation of an active agent, such as a steroid, is intended to include the drug compound or any salts, esters, isomers, conjugates, derivatives or prodrugs thereof.

The active agent generally is present in amounts about 0.01% to about 1%, by weight of the composition. However, other amounts are useful, depending on the potency of the active agent and the conditions to be treated.

In embodiments, a steroid present in the topical compositions is betamethasone dipropionate, which typically is administered in doses of about 0.001 mg/Kg body weight to about 0.5 mg/Kg body weight, to a subject in need thereof.

In embodiments, a steroid is betamethasone dipropionate, present in topical compositions in concentrations about 0.064% by weight, although higher or lower amounts may be used as desired, for example from about 0.01% to about 0.5% by weight, or from about 0.02% to about 0.07% by weight. In embodiments, a betamethasone compound used in the present application is present in compositions in amounts equivalent to about 0.025% to about 0.1%, or about 0.05%, by weight of betamethasone base.

In embodiments, compositions of the present application are formulated as emulsions, comprising an oily or hydrophobic phase, an aqueous or hydrophilic phase, and an emulsifier. When the oily phase is dispersed as droplets within an aqueous continuous phase, this is called an "oil-in-water" type of emulsion. When the aqueous phase is dispersed as droplets within an oily continuous phase, this is called an "water-in-oil" type of emulsion. In embodiments, the hydrophobic phase comprises about 0.5% to about 90% by weight of the composition. Compositions in the form of emulsions may be micro- or nano-emulsions. In embodiments, average particle sizes of the dispersed phase droplets are less than about 500 µm. In embodiments, average particle sizes of the dispersed phase droplets are less than about 2000 nm.

In embodiments, compositions of the present application include excipients including, but not limited to, one or more of carriers, emulsifiers, coemulsifiers, permeation or penetration enhancers, solvents, co-solvents, emollients, antioxidants, preservatives, buffering agents, gelling or thickening agents, polymers, surfactants, soothing agents, pH modifiers, solubilizers, humectants, emollients, moisturizers, oily bases, and the like.

"Emollients" are substances that soften and soothe the skin. They are used to correct dryness and scaling of the skin. Various emollients include, but are not limited to, oils of natural origin such as almond oil, coconut oil, olive oil, palm oil, peanut oil and the like, fatty acids such as lauric acid, myristic acid, palmitic acid, and stearic acid, monohydric alcohol esters of the fatty acids such as ethyl laurate, isopropyl laurate, ethyl myristate, n-propyl myristate, isopropyl myristate, ethyl palmitate, isopropyl palmitate, methyl palmitate, methyl stearate, ethyl stearate, isopropyl stearate, butyl stearate, isobutyl stearate, amyl stearate, and isoamyl stearate, glycols such as ethylene glycol, diethylene glycol, polyethylene glycol, and propylene glycol, branched aliphatic alcohols such as lauryl alcohol, myristyl alcohol, and stearyl alcohol, and any combinations thereof.

The term "carrier" denotes organic or inorganic ingredients, natural or synthetic, with which an active ingredient is combined to facilitate application of a composition. The term "carrier" includes, but is not limited to, one or more of water, acetone, alone or in combination with materials such as silicone fluids. The amounts of carrier may be about 5% to about 99% of the total weight of the composition. In embodiments, a carrier according to the present application comprises water. In embodiments, the carrier can comprise, in addition to water, water-immiscible substances such as any pharmaceutically acceptable fatty esters of natural fatty acids, triglycerides of animal or vegetable, medium chain triglycerides, mixtures of mono-, di- and/or triglycerides, waxes, hydrogenated vegetable oils, and mixtures thereof.

Examples of suitable polymers for use in the compositions include, but are not limited to carbomers, polyethylene glycols, acrylate polymers, methacrylate polymers, polyvinylpyrrolidones, copolymers based on butyl methacrylate and methyl methacrylate povidone, vinyl acetates, polyvinyl acetates, celluloses, gums, alginates, cellulose acetate phthalates, cellulose acetate butyrates, hydroxypropyl methyl cellulose phthalates, and the like. Examples include Carbopol® products, PEG 400, Eudragit® 100, Eudragit® RSPO, Eudragit® RLPO, Eudragit® ND40, Plasdone®, copolymers based on butyl methacrylate and methyl methacrylate (Plastoid® B), alkyl celluloses such as ethyl celluloses and methyl celluloses, hydroxyalkyl celluloses such as hydroxyethyl cellulose and hydroxypropyl cellulose, hydroxyalkyl alkyl celluloses such as hydroxypropyl methylcelluloses and hydroxybutyl methylcelluloses, gums such as xanthan gum, tragacanth, guar gum, locust bean gum, acacia, and the like. The amount of polymer may be about 0.5 to about 50% by weight of the total weight of the composition.

Other polymers that are useful include polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyglycolides, polysiloxanes, polyurethanes and copolymers thereof, cellulose ethers, cellulose esters, nitrocelluloses, polymers of acrylic and methacrylic esters, cellulose acetates, cellulose propionates, cellulose acetate butyrates, cellulose acetate phthalates, carboxylethyl celluloses, cellulose triacetates, cellulose sulphate sodium salts, poly(methyl ethacrylate), poly(ethylmethacrylate), poly(butylmethacrylate), poly(isobutylmethacrylate), poly(hexylmethacrylate), poly(isodecylmethacrylate), poly(lauryl methacrylate), poly (phenyl methacrylate), poly(methyl acrylate), poly(isopropyl acrylate), poly(isobutyl acrylate), poly(octadecyl acrylate), polyethylenes, polypropylenes, poly(ethylene glycol), poly(ethylene oxide), poly(ethylene terephthalate), poly(vinyl alcohol), poly(vinyl acetate), poly(vinyl chloride), polystyrenes, and the like, including any mixtures thereof.

Examples of other useful polymers include synthetic polymers, such as polymers of lactic acid and glycolic acid, polyanhydrides, poly(ortho ester), polyurethanes, poly(butyric acid), poly(valeric acid), poly(caprolactone), poly(hydroxybutyrate), poly(lactide-co-glycolide), poly(lactide-co-caprolactone), and natural polymers such as alginate and other polysaccharides that include but are not limited to arabinans, fructans, fucans, galactans, galacturonans, glucans, mannans, xylans (such as, for example, inulin), levan, fucoidan, carrageenan, galatocarolose, pectic acid, pectin, amylose, pullulan, glycogen, amylopectin, cellulose, dextran, pustulan, chitin, agarose, keratan, chondroitan, dermatan, hyaluronic acid, alginic acid, xanthan gum, starches, and various other natural homopolymers and heteropolymers, such as those containing one or more of aldoses, ketoses, acids or amines, erythrose, threose, ribose, arabinose, xylose, lyxose, allose, altrose, glucose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof, and including dextran and cellulose, collagen, albumin and other hydrophilic proteins, zein and other prolamines and hydrophobic proteins, copolymers and mixtures thereof.

The content of polymer may be about 0.01% to about 45% of the total weight of the composition.

Examples of suitable emulsifying agents include, but are not limited to, disodium cocoampho diacetate, oxyethylenated glyceryl cocoate (7 EO), PEG-20 hexadecenyl succinate, PEG-15 stearyl ether, ricinoleic monoethanolamide monosulfosuccinate salts, oxyethylenated hydrogenated ricinoleic triglyceride containing 60 ethylene oxide units such as the products sold by BASF under the trademarks Cremophor® RH 60 or Cremophor® RH 40 (polyoxyl 40 hydrogenated castor oil), polymers such as poloxamers, which are block copolymers of ethylene oxide and propylene oxide, and the nonsolid fatty substances at room temperature (that is to say, at temperatures ranging from about 20 to 35° C.) such as sesame oil, sweet almond oil, apricot stone oil, sunflower oil, octoxyglyceryl palmitate (or 2-ethylhexyl glyceryl ether palmitate), octoxyglyceryl behenate (or 2-ethylhexyl glyceryl ether behenate), dioctyl adipate, and tartrates of branched dialcohols. Sorbitan fatty acid esters are a series of mixtures of partial esters of sorbitol and its mono- and dianhydrides with fatty acids. Sorbitan esters include products sold as Arlacel® 20, Arlacel 40, Arlacel 60, Arlacel 80, Arlacel 83, Arlacel 85, Arlacel 987, Arlacel C, PEG-6 stearate and glycol stearate and PEG-32 stearate (Tefose® 63), and PEG-6 stearate and PEG-32 stearate (Tefose® 1500), and any mixtures thereof. Polyethylene glycol ethers of stearic acid are in another group of emulsifiers that can be used in the emulsions. Examples of polyethylene glycol ethers of stearic acid are steareth-2, steareth-4, steareth-6, steareth-7, steareth-10, steareth-11, steareth-13, steareth-15, steareth-20, polyethylene glycol ethers of stearyl alcohol (steareth 21), and any mixtures thereof. Other emulsifying agents include sodium lauryl sulphate, cetyl trialkyl ammonium bromide, polyoxyethylene sorbitan fatty acid esters, and any mixtures thereof. Amounts of emulsifier may be about 0.25% to about 45% of the total weight of the compositions.

Nonionic emulsifying agents include those that can be broadly defined as condensation products of long chain alcohols, e.g., $C_{8-30}$ alcohols, with sugar or to starch polymers, i.e., glycosides. Various sugars include, but are not limited to, glucose, fructose, mannose, and galactose, and various long chain alcohols include, but are not limited to, decyl alcohol, cetyl alcohol, stearyl alcohol, lauryl alcohol, myristyl alcohol, oleyl alcohol, and the like.

Other useful nonionic emulsifying agents include condensation products of alkylene oxides with fatty acids such as alkylene oxide esters of fatty acids. Other nonionic surfactants are the condensation products of alkylene oxides with 2 moles of fatty acids such as alkylene oxide diesters of fatty acids.

Emulsifying agents can also include any of a wide variety of cationic, anionic, zwitterionic, and amphoteric surfactants that are known in the art. Non-limiting examples of anionic emulsifying agents include alkyl isethionates, alkyl and alkyl ether sulfates and salts thereof, alkyl and alkyl ether phosphates and salts thereof, alkyl methyl taurates, and soaps (e.g., alkali metal salts and sodium or potassium salts) of fatty acids.

Examples of amphoteric and zwitterionic emulsifying agents include those which are broadly described as derivatives of aliphatic secondary and tertiary amines in which the aliphatic radical can be straight or branched chain, wherein one of the aliphatic substituents contains from about 8 to about 22 carbon atoms and one contains an anionic water solubilizing group, e.g., carboxy, sulfonate, sulfate, phosphate, or phosphonate. Specific examples include alkylimino acetates, iminodialkanoates and aminoalkanoates, imidazolinium and ammonium derivatives. Other suitable amphoteric and zwitterionic emulsifying agents include betaines, sultaines, hydroxysultaines, alkyl sarcosinates, and alkanoyl sarcosinates.

Silicone emulsifying agents are typically organically modified organopoly siloxanes, sometimes called silicone surfactants. Useful silicone emulsifying agents include dimethicone copolyols. These materials are polydimethyl siloxanes, which have been modified to include polyether side chains such as polyethylene oxide chains, polypropylene oxide chains, mixtures of these chains, and polyether chains containing moieties derived from both ethylene oxide and propylene oxide.

The amounts of emulsifier may be about 0.25% to about 45% of the total weight of the composition.

Co-emulsifiers or secondary emulsifying agents include polyoxylglycerides such as oleoyl macrogolglycerides (Labrafil® M 1944CS), linoleoyl macrogolglycerides (Labrafil® M 2125CS), caprylocaproyl macrogolglycerides (Labrasol®), cetyl alcohol (and) ceteth-20 (and) steareth-20 (Emulcire™ 61 WL 2659), glyceryl stearate (and) PEG-75 stearate (Gelot® 64), and any mixtures thereof.

A "permeation enhancer" or "penetration enhancer" is a component used to enhance the penetration rate of drugs through the skin or mucous membrane, such as by temporarily diminishing the impermeability of the skin or membrane. Permeation enhancers have also been called "accelerants" and "absorption promoters." There are numerous penetration enhancers that can be used. Various useful permeation enhancers include, for example: polyols and esters, including polyethylene glycol, polyethylene glycol monolaurate, and butanediol; sulfoxides, including dimethylsulfoxide and decylmethylsulfoxide; ethers, including diethylene glycol monoethyl ether (e.g., Transcutol® P) and diethylene glycol monomethyl ether; fatty acids, including lauric acid, oleic acid, and valeric acid; fatty acid esters, including isopropyl myristate, isopropyl palmitate, methyl propionate, and ethyl oleate; nitrogenous compounds including urea, dimethyl acetamide, dimethylformamide 2-pyrrolidone, ethanolamine, methyl-2-pyrrolidone, diethanolamine, and triethanolamine; terpenes; alkanones; organic acids, including salicylic acid, citric acid, and succinic acid; and any mixtures thereof. Further, one or more surfactants can also be used as a permeation or penetration enhancer. A permeation enhancer can be used in concentrations ranging from about 0.001-15%, or about 0.05-12%, or about 3-10%, of the total weight of the composition.

The term "preservative" refers to a natural or synthetic chemical that is added to products to prevent decomposition by microbial growth or by undesirable chemical changes. Preservatives can desirably be incorporated into a composition for protecting against the growth of potentially harmful microorganisms. While microorganisms tend to grow in an aqueous phase, microorganisms can also reside in a hydrophobic or oil phase. Suitable preservatives for compositions of the present invention include, but are not limited to, methylparaben, propylparaben, benzyl alcohol, chlorocresol, benzalkonium chloride, cetrimonium chloride, sodium edetate, boric acid, and any mixtures thereof. The amount of preservative may be about 0.25% to about 25% of the total weight of the composition.

Antioxidants are substances which inhibit oxidation or suppress reactions promoted by oxygen or peroxides. Antioxidants, especially lipid-soluble antioxidants, can be absorbed into the cellular membrane to neutralize oxygen radicals and thereby protect the membrane. Suitable antioxidants for compositions of the present invention include, but are not limited to, ascorbic acid (vitamin C), glutathione, lipoic acid, uric acid, carotenes, α-tocopherol (vitamin E), ubiquinol, butylated hydroxyanisole, butylated hydroxytoluene, sodium benzoate, propyl gallate (PG, E310), and tertiary-butylhydroquinone. The amounts of antioxidant may be about 0.01% to about 20%, of the total weight of the composition.

"Solvent" refers to components that aid in the dissolution of the drug in the formulation. Solvents serve to maintain a solution of the drug in the composition. Some solvents can also enhance percutaneous penetration of drug and/or act as humectants. For steroid drugs, solvents can include water-immiscible substances such as fatty esters of natural fatty acids, triglycerides of animal or vegetable, medium chain triglycerides, mixtures of mono-, di- and/or triglycerides, waxes, hydrogenated vegetable oils, and mixtures thereof. Some specific examples include castor oil, lanolin oil, citrate triisocetyl triglycerides having 10-18 carbon atoms, caprylic/capric triglycerides, coconut oil, corn oil, cottonseed oil, linseed oil, oil of mink, olive oil, palm oil, sunflower oil, nut oil, diethylene glycol monoethyl ether, diethylene glycol monomethyl ether, saturated paraffin oils, light or heavy mineral oils, vegetable oils or glycerides, and the like.

Some of the excipient substances described above can have more than one function in a formulation. For example, a substance can be both a solvent and a penetration enhancer, or both a solvent and a carrier. The categorizations of materials described above are not to be construed as limiting or restricting in any manner.

The compositions of the present application may be in the form of solutions, suspensions, emulsions, lotions, microemulsions, nanoemulsions, emulgels, gels, and the like. In embodiments, compositions may be in the form of an emulsion. The emulsion can be in the form of an oil-in-water type of emulsion or a water-in-oil type of emulsion. An aqueous-based emulsion, such as an oil-in-water emulsion, frequently has lower viscosity than other emulsion types and exhibits appreciable storage stability. Generally, oil-in-water emulsions have better skin feel properties, when applied to the skin, as these give sensations similar to an aqueous material.

The compositions can be applied directly onto affected areas of the skin, such as psoriatic plaques or dermatoses. Sprayable compositions, upon being sprayed, form droplets on the affected areas and, in embodiments, can provide release of the active agent for an extended duration of time.

Viscosities of aqueous-based emulsions of the present application frequently vary in the range of about 0.01-15 Pascal second, "Pa·s" (10-15,000 centipoise, "cP"), about 0.1-1.5 Pa·s (100-1,500 cP), or about 0.2-1 Pa·s (200-1,000 cP).

Aspects of the present application also provide dispensing devices for the topical delivery of the compositions onto the skin in the form of sprays. In embodiments, the present application provides devices, into which the compositions are filled, comprising a container, a dispenser, and a closure.

In embodiments, the closures used for packaging are made of a polymeric substance such as high-density polyethylene (HDPE), low-density polyethylene (LDPE), or resins. The closures are particularly in the form of caps that are fitted onto the containers to aid in providing support to the dispenser unit and/or to shield the contents of the container from the outside environment. Various container materials include, but are not limited to, tin plated steel, aluminum, stainless steel, plastics, and glass.

An example of a dispenser is a unit containing a pump that can be adapted to fit on any type of container, such as by threads that match threading on the container. The pump is capable of dispensing sprayable compositions of the present application through a dip tube extending into a container from an actuator and attached to a one-way valve, which releases the composition from an orifice in the actuator in the form of a spray. The valve may be a metering valve.

Various types of valves that can be used include, but are not limited to, continuous spray valves and metering valves. The actuators allow for easy opening and closing of the valve and are an integral part of a package. This also serves to aid in producing the required type of product discharge. Various types of actuators include but are not limited to spray actuators, foam actuators, solid-stream actuators, and special actuators.

In an embodiment a dispensing device may be a device comprising a container, having therein a pouch system or bag containing the product, optionally fitted with a dip tube and an actuator fitted with a valve wherein the container is filled with nitrogen gas or compressed air, surrounding the pouch or bag. Containers can be made of aluminum or tin plate and the pouch system or bag containing the product can be made of layers of polyethylene (PE), polypropylene (PP), polyethylene terephthalate (PET), and aluminum. Introduction of the composition into the system further increases the pressure of the system which is capable of dispensing the composition from the pouch into the actuator, fitted with a valve, such that the composition is consistently released in the form of a substantially uniform spray upon actuation. The pouch can have a dip tube therein, communicating with the actuator valve, to control the spray rate and reduce droplet size.

In embodiments, a dispensing device useful for dispensing the compositions of the present application provides spray rates and spray patterns, in a manner such that substantially uniform dosage is dispensed each time which appreciably covers the desired affected area of the skin onto which the composition is sprayed. The pump is intended to deliver the composition uniformly onto the skin. It covers a desired area of the skin and produces very fine uniform droplets, at a specified spray rate such as, but not limited to, about 20 to about 500 mg/actuation, or about 100 to about 200 mg/actuation. The device provides a reproducible spray pattern, such as circular, frequently covering an area of about 0.1 to about 10 $cm^2$ depending on the distance from the application site.

About 2-6 priming actuations can be required for a new pump to reproducibly dispense the compositions. In a specific embodiment, about 160 μL of a formulation is dispensed, per actuation of the pump. Devices frequently provide a reproducible distribution of droplets, in distributions where about 90% of the droplets have sizes ranging from about 1 to about 500 μm.

The orifice is sized to control the droplet sizes of the dispensed product. The orifice size also affects providing of a uniform characteristic spray pattern.

In embodiments, the compositions useful in treating psoriasis may be packaged in a bottle fitted with an attached spray pump closure that can be mechanically actuated by a patient or caregiver, to apply the composition to the affected skin (i.e., a pump-type spray closure).

In embodiments, a spray formulation of the present application can be applied in an essentially easier and more exact way than creams and ointments can be applied, since for the spray application it is only necessary to spray a given volume, whereas the application of the semi-solid products requires an easily accessible and visual estimation of the cream amount or the ointment amount. Further, smearing and soiling of clothing can more easily be avoided on large surface areas. For the spray compositions, spreading and rubbing are not necessarily required, contrary to cream and ointment products, since the layer formed on the body surface by evaporation or vaporization of the liquid already has an ideal fine dispersion of active agent; hence 'pressure pain' will not occur from the topical application of spray compositions of the present application.

In an aspect, aqueous based emulsion sprayable formulations of the present application also permit applying a medicament by a method whereby the area of application is contacted by only the spray.

In an aspect, topical application of compositions of the present application forms a depot on the skin without forming an occlusive film, thereby extending the duration of active agent action while allowing 'breathing' of the skin.

Aspects of the present application further provide processes for preparing compositions that can be filled into suitable dispensing devices. In embodiments, processes comprise:

a) preparing a composition comprising the active agent and one or more suitable excipients, and b) filling a desired quantity of the composition into a dispensing device.

In embodiments, processes for preparing topical compositions comprising betamethasone as an active agent and excipients comprise:

a) heating a mixture comprising an emulsifying agent and a solvent to obtain an oily phase;

b) optionally, admixing an antioxidant and/or preservative into the oily phase of a);

c) admixing an active agent with a penetration enhancer;

d) admixing the material of c) with material of a) or b);

e) dissolving a polymer in an aqueous phase;

f) admixing the oily phase of d) slowly with the aqueous phase of e) with continuous mixing; and g) homogenizing the mixture of f), followed by cooling.

In embodiments, compositions of the present application have pH values ranging from about 3 to about 7, or about 3.5 to about 6.

In embodiments, the oily phase for an emulsion is a mixture of emulsifying agents and a solvent.

In embodiments, betamethasone spray compositions of the present application exhibit a comparable drug dissolution profile to that of a commercial DIPROLENE® lotion, a product of Schering Corporation, containing 0.05% betamethasone (in the form of betamethasone dipropionate), water, isopropyl alcohol (30%), hydroxypropyl cellulose, propylene glycol, sodium phosphate, phosphoric acid, and sodium hydroxide.

Figure 3:
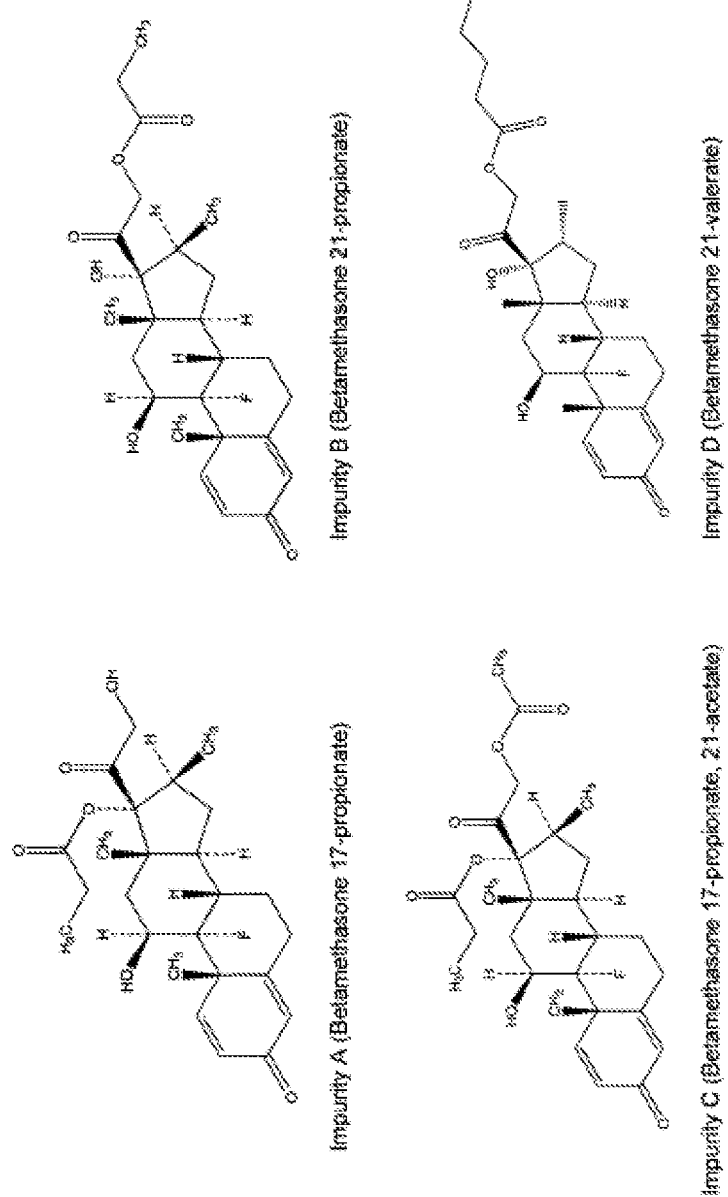
FIG. 3 shows structural formulas for certain betamethasone dipropionate-related impurities.

In embodiments, betamethasone propionate formulations of the present application may contain any one or more of impurities, such as impurity A (betamethasone 17-propionate) in amounts not more than about 5%, impurity B (betamethasone 21-propionate) in amounts not more than about 2%, impurity C (betamethasone 17-propionate 21-acetate) in amounts not more than about 1%, and impurity D (betamethasone 21-valerate) in amounts not more than about 1%, these impurities having the structures shown in FIG. 3, and any other drug-related impurities, in amounts such that any such impurities do not substantially adversely affect the safety of the composition. Impurities A and B are primarily observed during stability studies of a formulation, and impurities C and D are generally process-related impurities from synthesis of the drug. The above impurity limits are expressed as percentages of the label drug content in the formulation.

The following examples are provided to illustrate certain specific aspects and embodiments of the application, and are not to be construed as limiting the scope of the application in any manner. In the examples, the active agent betamethasone dipropionate used has a particle size distribution wherein half of the particles have sizes less than about 50 μm, and 90% of the particles have sizes less than about 300 μm.

Example 1: Betamethasone Spray Formulations

| | Wt. Percent | |
|---|---|---|
| Ingredient | A | B |
| Betamethasone dipropionate | 0.064 | 0.064 |
| Polyethylene glycol and ethylene glycol palmitostearate | 7.5 | 7.5 |
| Mineral oil | 7.06 | 7.06 |
| Oleoyl polyoxylglycerides | 2.94 | 2.94 |
| Diethyleneglycol monoethyl ether | 5 | 5 |
| Propylparaben | 0.8 | 0.8 |
| Methylparaben | 0.2 | 0.2 |
| Butylated hydroxytoluene | 0.05 | 0.05 |
| Hydroxyethyl cellulose | 0.1 | — |
| Xanthan gum | — | 0.1 |
| Water | 76.3 | 76.3 |

Manufacturing process:

a) Polyethylene glycol and ethylene glycol palmitostearate, oleoyl polyoxyglycerides, and mineral oil are mixed and heated to about 50-70° C.

b) Propylparaben, methylparaben, and butylated hydroxytoluene are mixed with the liquid of a) with continuous stirring at about 50-70° C.

c) Betamethasone dipropionate is mixed with diethylene glycol monoethyl ether.

d) The material of c) is mixed with the material of b).

e) Hydroxyethyl cellulose or xanthan gum is dissolved in water.

f) The oily phase of d) is added slowly to the aqueous phase of e), or vice versa, at about 50-70° C. with continuous stirring.

g) The mixture of f) is homogenized and allowed to cool to ambient temperature.

Comparative in vitro dissolution profile testing, showing drug release from Formulation A and Formulation B, and a commercial reference product, is conducted. The reference product is DIPROLENE® lotion. The test procedure is as described below.

A Franz diffusion cell is fitted with a polysulphone 0.2 μm membrane clamped between the donor and receptor compartments. The receptor media is a mixture of ethanol and water (20:80 by volume) with a replacement volume of 12.0 mL, sampling volume of 2.0 mL at the times 30, 60, 120, 240, and 360 minutes, and the temperature maintained at 32±0.5° C. About 200 mg of the formulation is applied uniformly over the membrane using a syringe. The donor compartment is covered using Parafilm® (hydrocarbon wax and polyolefin blend). Receptor fluid is analyzed for the drug, using high performance liquid chromatography (HPLC).

TABLE 1

| | Cumulative % of Drug Released | | |
|---|---|---|---|
| Minutes | DIPROLENE | Formulation A | Formulation B |
| 30 | 28.6 | 1.6 | 1.0 |
| 60 | 66.5 | 3.3 | 3.7 |
| 120 | 100.3 | 5.65 | 8.2 |
| 240 | 117.9 | 10.8 | 15.6 |
| 360 | 123.8 | 15.5 | 22.4 |

Drug release from DIPROLENE lotion is rapid. However, from Formulation A and Formulation B, betamethasone release is slow and sustained over several hours. The results are plotted in FIG. 1. A release lag time remains below 30 minutes in all of the compositions tested, and is assumed to be contributed mainly from the polymeric membrane used for release testing. The rates of drug release, fitted to the Higuchi equation, for Formulations A and B, are shown in Table 2.

TABLE 2

| Formulation | Release Rate (μg/cm$^2$ · min$^{0.5}$) | Release Lag Time (minutes) | Regression Coefficient |
|---|---|---|---|
| A | 1.023 | 20.4 | 0.984 |
| B | 1.587 | 28.2 | 0.993 |

The prepared formulations, filled into closed containers, are exposed to the stability testing conditions 25° C. and 60% relative humidity (RH), 30° C. and 65% RH, and 40° C. and 75% RH for three months, and analyses at various storage points are shown in Tables 3 and 4, where the values are percentages of the label drug content.

TABLE 3

| | Formulation A | | | | | |
|---|---|---|---|---|---|---|
| Storage | | | Impurities | | | |
| Conditions | | Drug Assay | A | B | C | D | Total |
| Initial | — | 99.08 | — | — | — | — | 2.09 |
| 1 Month | 25° C. | 100.7 | 0.63 | 0.27 | ND | ND | 1.34 |
| | 30° C. | 100 | 0.73 | 0.28 | ND | ND | 1.48 |
| | 40° C. | 99.36 | 0.92 | 0.25 | ND | ND | 1.59 |
| 2 Months | 25° C. | 103.5 | 0.78 | 0.39 | ND | ND | 1.61 |
| | 30° C. | 102.4 | 0.89 | 0.3 | ND | ND | 1.77 |
| | 40° C. | 100.7 | 1.34 | 0.4 | ND | ND | 2.62 |

TABLE 3-continued

Formulation A

| Storage | | Impurities | | | | |
|---|---|---|---|---|---|---|
| Conditions | Drug Assay | A | B | C | D | Total |
| 3 Months 25° C. | 101.3 | 0.57 | 0.24 | ND | ND | 1.54 |
| 30° C. | 101.6 | 0.76 | 0.26 | ND | ND | 1.72 |
| 40° C. | 100.6 | 1.52 | 0.34 | ND | ND | 2.18 |

ND = not detected.

TABLE 4

Formulation B

| Storage | | Drug Assay | Impurities | | | | |
|---|---|---|---|---|---|---|---|
| | | | A | B | C | D | Total |
| Initial | — | 101.81 | — | — | — | — | 1.52 |
| 1 Month | 25° C. | 99.5 | 0.32 | 0.26 | ND | ND | 0.75 |
| | 30° C. | 103.2 | 0.33 | 0.29 | ND | ND | 0.61 |
| | 40° C. | 103.4 | 0.41 | 0.35 | ND | ND | 0.76 |
| 2 Months | 25° C. | 102.3 | 0.34 | 0.32 | ND | ND | 1.04 |
| | 30° C. | 102.3 | 0.34 | 0.31 | ND | ND | 0.65 |
| | 40° C. | 102.5 | 0.59 | 0.36 | ND | ND | 0.95 |
| 3 Months | 25° C. | 99.4 | 0.31 | 0.29 | ND | ND | 0.99 |
| | 30° C. | 99.6 | 0.37 | 0.32 | ND | ND | 1.1 |
| | 40° C. | 98.2 | 0.74 | 0.33 | ND | ND | 1.83 |

ND = not detected.

Example 2: Betamethasone Spray Formulations

| | Wt. Percent | | | | |
|---|---|---|---|---|---|
| Ingredient | C | D | E | F | G |
| Betamethasone dipropionate | 0.032 | 0.064 | 0.064 | 0.064 | 0.064 |
| PEG-6 palmitostearate (and) ethylene glycol palmitostearate (and) PEG-32 palmitostearate | 7.5 | 7.5 | 7.5 | 7.5 | 7.5 |
| Mineral oil | 7.06 | 7.06 | 7.06 | 7.06 | 7.06 |
| Oleoyl polyoxylglycerides | 2.94 | 2.94 | 2.94 | 2.94 | 2.94 |
| Diethyleneglycol monoethyl ether | 3 | 5 | 7 | 3 | 10 |
| Propylparaben | 0.8 | 0.8 | 0.8 | 0.8 | 0.8 |
| Methylparaben | 0.2 | 0.2 | 0.2 | 0.2 | 0.2 |
| Butylated hydroxytoluene | 0.05 | 0.05 | 0.05 | 0.05 | 0.05 |
| Hydroxyethyl cellulose | 0.1 | 0.1 | 0.1 | 0.1 | 0.1 |
| Water | 78.31 | 76.28 | 74.28 | 78.28 | 71.28 |

Manufacturing process:

a) Polyethylene glycol and ethylene glycol palmitostearate, oleoyl polyoxyglycerides, and mineral oil are mixed and heated to about 50-70° C.

b) Propylparaben, methylparaben, and butylated hydroxytoluene are mixed with the liquid of a) with continuous stirring at about 50-70° C.

c) Betamethasone dipropionate is mixed with diethyleneglycol monoethyl ether.

d) Material of c) is mixed with material of b).

e) Hydroxyethyl cellulose is dissolved in water.

f) The oily phase of d) is slowly added to the aqueous phase of e), or vice versa, at about 50-70° C. with continuous stirring.

g) The mixture of f) is homogenized and allowed to cool to ambient temperature.

A stability study is conducted for Formulation D, involving storing the formulation for 3 months in closed containers at the conditions 25° C. and 60% RH, 30° C. and 65% RH, and 40° C. and 75% RH. All samples remain off-white homogenous emulsions with no phase separation. Drug assay values are within the specified limits of 90-110% of the label drug content for all samples, as shown in Table 5, where all values are percentages of the label drug content. The pH of the samples remains between 3 and 6. Viscosity values, measured at 100 rpm using a Brookfield CAP 2000+ viscometer, remain close to the original values for all samples.

TABLE 5

| Storage | | Drug Assay | Impurities | | | | |
|---|---|---|---|---|---|---|---|
| | | | A | B | C | D | Total |
| Initial | — | 101.6 | — | — | — | — | 0.14 |
| 1 Month | 25° C. | 102.6 | 0.56 | 0.03 | 0.09 | ND | 0.68 |
| | 30° C. | 100.7 | 0.63 | 0.03 | 0.09 | ND | 0.74 |
| | 40° C. | 97.7 | 1.32 | 0.04 | 0.09 | ND | 1.45 |
| 2 Months | 25° C. | 100.9 | 0.77 | ND | 0.08 | ND | 0.85 |
| | 30° C. | 100.7 | 0.91 | 0.02 | 0.08 | ND | 1.02 |
| | 40° C. | 98.7 | 2.04 | 0.11 | 0.07 | ND | 2.22 |
| 3 Months | 25° C. | 101.3 | 1.04 | 0.05 | 0.02 | ND | 1.17 |
| | 30° C. | 100.5 | 1.22 | 0.05 | 0.02 | ND | 1.29 |
| | 40° C. | — | 2.92 | 0.26 | 0.01 | ND | 3.24 |

ND = not detected.

Example 3: Betamethasone Spray Formulations

| | Wt. Percent | | | |
|---|---|---|---|---|
| Ingredient | H | I | J | K |
| Betamethasone dipropionate | 0.032 | 0.064 | 0.064 | 0.064 |
| PEG-6 palmitostearate (and) ethylene glycol palmitostearate (and) PEG-32 palmitostearate | 7.5 | 7.5 | 7.5 | 7.5 |
| Mineral oil | 7.06 | 7.06 | 7.06 | 7.06 |
| Oleoyl polyoxylglycerides | 2.94 | 2.94 | 2.94 | 2.94 |
| Diethyleneglycol monoethyl ether | 3 | 5 | 7 | 3 |
| Propylparaben | 0.8 | 0.8 | 0.8 | 0.8 |
| Methylparaben | 0.2 | 0.2 | 0.2 | 0.2 |
| Butylated hydroxytoluene | 0.05 | 0.05 | 0.05 | 0.05 |
| Xanthan gum | 0.1 | 0.1 | 0.1 | 0.1 |
| Water | 78.31 | 76.28 | 74.28 | 78.28 |

Manufacturing process:

a) Polyethylene glycol and ethylene glycol palmitostearate, oleoyl polyoxyglycerides, and mineral oil are mixed and heated to about 50-70° C.

b) Propylparaben, methylparaben, and butylated hydroxytoluene are mixed with the liquid of a) with continuous stirring at about 50-70° C.

c) Betamethasone dipropionate is mixed with diethyleneglycol monoethyl ether.

d) The material of c) is mixed with the material of b).

e) Xanthan gum is dissolved in water.

f) The oily phase of d) is slowly added to the aqueous phase of e), or vice versa, at about 50-70° C. with continuous stirring.

g) The mixture of (f) is homogenized and allowed to cool to ambient temperature.

Example 4: Betamethasone Spray Formulations

|  | Wt. Percent | | | | |
| --- | --- | --- | --- | --- | --- |
| Ingredient | L | M | N | O | P |
| Betamethasone dipropionate | 0.064 | 0.064 | 0.064 | 0.064 | 0.064 |
| PEG-6 palmitostearate (and) ethylene glycol palmitostearate (and) PEG-32 palmitostearate | 1.5 | — | — | — | 1.5 |
| PEG-6 stearate and PEG-32 stearate | — | — | 1.5 | 1.5 | — |
| Sorbitan stearate | 2.5 | 2.5 | 2.5 | 2.5 | 2.5 |
| PEG ether of stearyl alcohol | — | 2.22 | — | — | — |
| Mineral oil | 7.06 | 7.06 | 7.06 | 7.06 | 7.06 |
| Oleoyl polyoxylglycerides | 2.94 | 2.94 | 2.94 | — | — |
| Cetyl alcohol (and) ceteth 20 (and) steareth 20 | — | — | — | 1 | 1 |
| Diethyleneglycol monoethyl ether | 10 | 5 | 5 | 5 | 5 |
| Propylparaben | 0.8 | 0.8 | 0.8 | 0.8 | 0.8 |
| Methylparaben | 0.2 | 0.2 | 0.2 | 0.2 | 0.2 |
| Butylated hydroxytoluene | 0.05 | 0.05 | 0.05 | 0.05 | 0.05 |
| Hydroxyethyl cellulose | 0.1 | 0.1 | 0.1 | 0.1 | 0.1 |
| Water | 76.35 | 74.85 | 79.13 | 79.85 | 81.79 |

Manufacturing process:

a) Polyethylene glycol (and) ethylene glycol palmitostearate (and) PEG-32 palmitostearate, PEG-6 stearate and PEG-32 stearate, sorbitan stearate, PEG ether of stearyl alcohol, mineral oil, oleoyl polyoxyglycerides, and cetyl alcohol (and) ceteth 20 (and) steareth 20, as required, are mixed and heated to about 50-70° C.

b) Propylparaben, methylparaben, and butylated hydroxytoluene are mixed with the liquid of a) with continuous stirring at about 50-70° C.

c) Betamethasone dipropionate is mixed with diethyleneglycol monoethyl ether.

d) The material of c) is mixed with the material of b).

e) Hydroxyethyl cellulose is dissolved in water.

f) The oily phase of d) is added slowly to the aqueous phase of e), or vice versa, at about 50-70° C. with continuous stirring.

g) The mixture of f) is homogenized and allowed to cool to ambient temperature.

Example 5: Mometasone Spray Formulations

|  | Wt. Percent | |
| --- | --- | --- |
| Ingredient | AB 1 | AB 2 |
| Mometasone furoate | 0.1 | 0.1 |
| Polyethylene glycol and ethylene glycol palmitostearate | 7.5 | 7.5 |
| Mineral oil | 7.06 | 7.06 |
| Oleoyl polyoxylglycerides | 2.94 | 2.94 |
| Diethyleneglycol monoethyl ether | 5 | 5 |
| Propylparaben | 0.8 | 0.8 |
| Methylparaben | 0.2 | 0.2 |
| Butylated hydroxytoluene | 0.05 | 0.05 |
| Hydroxyethyl cellulose | 0.1 | — |
| Xanthan gum | — | 0.1 |
| Water | 76.25 | 76.25 |

Manufacturing process:

a) Polyethylene glycol and ethylene glycol palmitostearate, oleoyl polyoxyglycerides, and mineral oil are mixed and heated at about 50-70° C.

b) Propylparaben, methylparaben, and butylated hydroxytoluene are mixed with the liquid of a) with continuous stirring at about 50-70° C.

c) Mometasone furoate is mixed with diethyleneglycol monoethyl ether.

d) The material of c) is mixed with the material of b).

e) Hydroxyethyl cellulose or xanthan gum is dissolved in water.

f) The oily phase of d) is added slowly to the aqueous phase of e), or vice versa, at about 50-70° C. with continuous stirring.

g) The mixture of f) is homogenized and allowed to cool to ambient temperature.

Example 6: Halobetasol Spray Formulations

|  | Wt. Percent | |
| --- | --- | --- |
| Ingredient | AB 3 | AB 4 |
| Halobetasol propionate | 0.05 | 0.05 |
| Polyethylene glycol and ethylene glycol palmitostearate | 7.5 | 7.5 |
| Mineral oil | 7.06 | 7.06 |
| Oleoyl polyoxylglycerides | 2.94 | 2.94 |
| Diethyleneglycol monoethyl ether | 5 | 5 |
| Propylparaben | 0.8 | 0.8 |
| Methylparaben | 0.2 | 0.2 |
| Butylated hydroxytoluene | 0.05 | 0.05 |
| Hydroxyethyl cellulose | 0.1 | — |
| Xanthan gum | — | 0.1 |
| Water | 76.3 | 76.3 |

Manufacturing process:

a) Polyethylene glycol and ethylene glycol palmitostearate, oleoyl polyoxyglycerides, and mineral oil are mixed and heated at about 50-70° C.

b) Propylparaben, methylparaben, and butylated hydroxytoluene are mixed with the liquid of a) with continuous stirring at about 50-70° C.

c) Halobetasol propionate is mixed with diethyleneglycol monoethyl ether.

d) The material of c) is mixed with the material of b).

e) Hydroxyethyl cellulose or xanthan gum is dissolved in water.

f) The oily phase of d) is added slowly to the aqueous phase of e), or vice versa, at about 50-70° C. with continuous stirring.

g) The mixture of f) is homogenized and allowed to cool to ambient temperature.

Example 7: Triamcinolone Spray Formulations

|  | Wt. Percent | |
| --- | --- | --- |
| Ingredient | AB 5 | AB 6 |
| Triamcinolone acetonide | 0.1 | 0.1 |
| Polyethylene glycol and ethylene glycol palmitostearate | 7.5 | 7.5 |
| Mineral oil | 7.06 | 7.06 |
| Oleoyl polyoxylglycerides | 2.94 | 2.94 |
| Diethyleneglycol monoethyl ether | 5 | 5 |
| Propylparaben | 0.8 | 0.8 |
| Methylparaben | 0.2 | 0.2 |

-continued

|                          | Wt. Percent |      |
|--------------------------|------|------|
| Ingredient               | AB 5 | AB 6 |
| Butylated hydroxytoluene | 0.05 | 0.05 |
| Hydroxyethyl cellulose   | 0.1  | —    |
| Xanthan gum              | —    | 0.1  |
| Water                    | 76.25| 76.25|

Manufacturing process:

a) Polyethylene glycol and ethylene glycol palmitostearate, oleoyl polyoxyglycerides, and mineral oil are mixed and heated to about 50-70° C.

b) Propylparaben, methylparaben, and butylated hydroxytoluene are mixed with the liquid of a) with continuous stirring at about 50-70° C.

c) Triamcinolone acetonide is mixed with diethyleneglycol monoethyl ether.

d) The material of c) is mixed with the material of b).

e) Hydroxyethyl cellulose or xanthan gum is dissolved in water.

f) The oily phase of d) is added slowly to the aqueous phase of e), or vice versa, at about 50-70° C. with continuous stirring.

g) The mixture of f) is homogenized and allowed to cool to ambient temperature.

Example 8: Hydrocortisone Spray Formulations

|                                                     | Wt. Percent |      |
|-----------------------------------------------------|------|------|
| Ingredient                                          | AB 7 | AB 8 |
| Hydrocortisone butyrate                             | 0.1  | 0.1  |
| Polyethylene glycol and ethylene glycol palmitostearate | 7.5  | 7.5  |
| Mineral oil                                         | 7.06 | 7.06 |
| Oleoyl polyoxylglycerides                           | 2.94 | 2.94 |
| Diethyleneglycol monoethyl ether                    | 5    | 5    |
| Propylparaben                                       | 0.8  | 0.8  |
| Methylparaben                                       | 0.2  | 0.2  |
| Butylated hydroxytoluene                            | 0.05 | 0.05 |
| Hydroxyethyl cellulose                              | 0.1  | —    |
| Xanthan gum                                         | —    | 0.1  |
| Water                                               | 76.25| 76.25|

Manufacturing process:

a) Polyethylene glycol and ethylene glycol palmitostearate, oleoyl polyoxyglycerides, and mineral oil are mixed and heated to about 50-70° C.

b) Propylparaben, methylparaben, and butylated hydroxytoluene are mixed with the liquid of a) with continuous stirring at about 50-70° C.

c) Hydrocortisone butyrate is mixed with diethyleneglycol monoethyl ether.

d) The material of c) is mixed with the material of b).

e) Hydroxyethyl cellulose or xanthan gum is dissolved in water.

f) The oily phase of d) is added slowly to the aqueous phase of e), or vice versa, at about 50-70° C. with continuous stirring.

g) The mixture of f) is homogenized and allowed to cool to ambient temperature.

Example 9: Betamethasone Spray Formulations

|                                                     | Wt. Percent |       |
|-----------------------------------------------------|------|-------|
| Ingredient                                          | AB 9 | AB 10 |
| Betamethasone valerate                              | 0.05 | 0.05  |
| Polyethylene glycol and ethylene glycol palmitostearate | 7.5  | 7.5   |
| Mineral oil                                         | 7.06 | 7.06  |
| Oleoyl polyoxylglycerides                           | 2.94 | 2.94  |
| Diethyleneglycol monoethyl ether                    | 5    | 5     |
| Propylparaben                                       | 0.8  | 0.8   |
| Methylparaben                                       | 0.2  | 0.2   |
| Butylated hydroxytoluene                            | 0.05 | 0.05  |
| Hydroxyethyl cellulose                              | 0.1  | —     |
| Xanthan gum                                         | —    | 0.1   |
| Water                                               | 76.3 | 76.3  |

Manufacturing process:

a) Polyethylene glycol and ethylene glycol palmitostearate, oleoyl polyoxyglycerides, and mineral oil are mixed and heated to about 50-70° C.

b) Propylparaben, methylparaben, and butylated hydroxytoluene are mixed with the liquid of a) with continuous stirring at about 50-70° C.

c) Betamethasone valerate is mixed with diethyleneglycol monoethyl ether.

d) The material of c) is mixed with the material of b).

e) Hydroxyethyl cellulose or xanthan gum is dissolved in water.

f) The oily phase of d) is added slowly to the aqueous phase of e), or vice versa, at about 50-70° C. with continuous stirring.

g) The mixture of f) is homogenized and allowed to cool to ambient temperature.

Example 10: Fluocinolone Spray Formulations

|                                                     | Wt. Percent |       |
|-----------------------------------------------------|-------|-------|
| Ingredient                                          | AB 11 | AB 12 |
| Fluocinolone acetonide                              | 0.05  | 0.05  |
| Polyethylene glycol and ethylene glycol palmitostearate | 7.5   | 7.5   |
| Mineral oil                                         | 7.06  | 7.06  |
| Oleoyl polyoxylglycerides                           | 2.94  | 2.94  |
| Diethyleneglycol monoethyl ether                    | 5     | 5     |
| Propylparaben                                       | 0.8   | 0.8   |
| Methylparaben                                       | 0.2   | 0.2   |
| Butylated hydroxytoluene                            | 0.05  | 0.05  |
| Hydroxyethyl cellulose                              | 0.1   | —     |
| Xanthan gum                                         | —     | 0.1   |
| Water                                               | 76.3  | 76.3  |

Manufacturing process:

a) Polyethylene glycol and ethylene glycol palmitostearate, oleoyl polyoxyglycerides, and mineral oil are mixed and heated to about 50-70° C.

b) Propylparaben, methylparaben, and butylated hydroxytoluene are mixed with the liquid of a) with continuous stirring at about 50-70° C.

c) Fluocinolone acetonide is mixed with diethyleneglycol monoethyl ether.

d) The material of c) is mixed with the material of b).

e) Hydroxyethyl cellulose or xanthan gum is dissolved in water.

f) The oily phase of d) is added slowly to the aqueous phase of e), or vice versa, at about 50-70° C. with continuous stirring.

g) The mixture of f) is homogenized and allowed to cool to ambient temperature.

Example 11: Desonide Spray Formulations

|  | Wt. Percent | |
| --- | --- | --- |
| Ingredient | AB 13 | AB 14 |
| Desonide | 0.05 | 0.05 |
| Polyethylene glycol and ethylene glycol palmitostearate | 7.5 | 7.5 |
| Mineral oil | 7.06 | 7.06 |
| Oleoyl polyoxylglycerides | 2.94 | 2.94 |
| Diethyleneglycol monoethyl ether | 5 | 5 |
| Propylparaben | 0.8 | 0.8 |
| Methylparaben | 0.2 | 0.2 |
| Butylated hydroxytoluene | 0.05 | 0.05 |
| Hydroxyethyl cellulose | 0.1 | — |
| Xanthan gum | — | 0.1 |
| Water | 76.3 | 76.3 |

Manufacturing process:

a) Polyethylene glycol and ethylene glycol palmitostearate, oleoyl polyoxyglycerides, and mineral oil are mixed and heated to about 50-70° C.

b) Propylparaben, methylparaben, and butylated hydroxytoluene are mixed with the liquid of a) with continuous stirring at about 50-70° C.

c) Desonide is mixed with diethyleneglycol monoethyl ether.

d) The material of c) is mixed with the material of b).

e) Hydroxyethyl cellulose or xanthan gum is dissolved in water.

f) The oily phase of d) is added slowly to the aqueous phase of e), or vice versa, at about 50-70° C. with continuous stirring.

g) The mixture of f) is homogenized and allowed to cool to ambient temperature.

Example 12: Methylprednisolone Spray Formulations

|  | Wt. Percent | |
| --- | --- | --- |
| Ingredient | AB 15 | AB 16 |
| Methylprednisolone | 0.1 | 0.1 |
| Polyethylene glycol and ethylene glycol palmitostearate | 7.5 | 7.5 |
| Mineral oil | 7.06 | 7.06 |
| Oleoyl polyoxylglycerides | 2.94 | 2.94 |
| Diethyleneglycol monoethyl ether | 5 | 5 |
| Propylparaben | 0.8 | 0.8 |
| Methylparaben | 0.2 | 0.2 |
| Butylated hydroxytoluene | 0.05 | 0.05 |
| Hydroxyethyl cellulose | 0.1 | — |
| Xanthan gum | — | 0.1 |
| Water | 76.25 | 76.25 |

Manufacturing process:

a) Polyethylene glycol and ethylene glycol palmitostearate, oleoyl polyoxyglycerides, and mineral oil are mixed and heated to about 50-70° C.

b) Propylparaben, methylparaben, and butylated hydroxytoluene are mixed with the liquid of a) with continuous stirring at about 50-70° C.

c) Methylprednisolone is mixed with diethyleneglycol monoethyl ether.

d) The material of c) is mixed with the material of b).

e) Hydroxyethyl cellulose or xanthan gum is dissolved in water.

f) The oily phase of d) is added slowly to the aqueous phase of e), or vice versa, at about 50-70° C. with continuous stirring.

g) The mixture of f) is homogenized and allowed to cool to ambient temperature.

Example 13: Alclometasone Spray Formulations

|  | Wt. Percent | |
| --- | --- | --- |
| Ingredient | AB 17 | AB 18 |
| Alclometasone dipropionate | 0.005 | 0.005 |
| Polyethylene glycol and ethylene glycol palmitostearate | 7.5 | 7.5 |
| Mineral oil | 7.06 | 7.06 |
| Oleoyl polyoxylglycerides | 2.94 | 2.94 |
| Diethyleneglycol monoethyl ether | 5 | 5 |
| Propylparaben | 0.8 | 0.8 |
| Methylparaben | 0.2 | 0.2 |
| Butylated hydroxytoluene | 0.05 | 0.05 |
| Hydroxyethyl cellulose | 0.1 | — |
| Xanthan gum | — | 0.1 |
| Water | 76.3 | 76.3 |

Manufacturing process:

a) Polyethylene glycol and ethylene glycol palmitostearate, oleoyl polyoxyglycerides, and mineral oil are mixed and heated to about 50-70° C.

b) Propylparaben, methylparaben, and butylated hydroxytoluene are mixed with the liquid of a) with continuous stirring at about 50-70° C.

c) Alclometasone dipropionate is mixed with diethyleneglycol monoethyl ether.

d) The material of c) is mixed with the material of b).

e) Hydroxyethyl cellulose or xanthan gum is dissolved in water.

f) The oily phase of d) is added slowly to the aqueous phase of e), or vice versa, at about 50-70° C. with continuous stirring.

g) The mixture of f) is homogenized and allowed to cool to ambient temperature.

Example 14: Betamethasone Spray Formulations

|  | Wt. Percent | |
| --- | --- | --- |
| Ingredient | AB 19 | AB 20 |
| Betamethasone dipropionate | 0.05 | 0.05 |
| Ethanol | 74.89 | 7 |
| Isopropyl myristate | 12 | 10 |
| Transcutol ® P | 5 | 12 |
| Mineral oil | 7.06 | 69.95 |
| Acrylic polymer | 1 | 1 |

Manufacturing process:

a) Acrylic polymer is dissolved in ethanol.

b) Betamethasone dipropionate is dissolved in a mixture of isopropyl myristate, mineral oil, and Transcutol P, with stirring.

c) The mixtures of a) and b) are combined with continuous stirring to obtain the product.

Example 15: Mometasone Spray Formulations

| Ingredient | Wt. Percent | |
|---|---|---|
| | AB 21 | AB 22 |
| Mometasone furoate | 0.1 | 0.1 |
| Polyethylene glycol and ethylene glycol palmitostearate | 7.5 | 7.5 |
| Mineral oil | 7.06 | 7.06 |
| Oleoyl polyoxylglycerides | 2.94 | 2.94 |
| Transcutol P | 5 | 12 |
| Propylene glycol | 7 | 3 |
| Propylparaben | 0.8 | 0.8 |
| Methylparaben | 0.2 | 0.2 |
| Butylated hydroxytoluene | 0.05 | 0.05 |
| Hydroxyethyl cellulose | 0.1 | — |
| Xanthan gum | — | 0.1 |
| Water | 69.25 | 66.25 |

Manufacturing process:

a) Polyethylene glycol and ethylene glycol palmitostearate, oleoyl polyoxyglycerides, and mineral oil are mixed and heated to about 50-70° C.

b) Propylparaben, methylparaben, and butylated hydroxytoluene are mixed with the liquid of a) with continuous stirring at about 50-70° C.

c) Mometasone furoate is mixed with Transcutol P.

d) The material of (c) is mixed with the material of b).

e) Hydroxyethyl cellulose or xanthan gum is dissolved in water.

f) The oily phase of d) is added slowly to the aqueous phase of e), or vice versa, at about 50-70° C. with continuous stirring.

g) The mixture of f) is homogenized and allowed to cool to ambient temperature.

Example 16: Dermal Toxicity Testing

A toxicity study is conducted, involving once-daily dermal administration of 0.025 and 0.05% betamethasone dipropionate sprays prepared in Example 3 (Formulations C and D) at doses of 0.5 and 1 mg/Kg/day for 28 days, to Sprague-Dawley rats. The formulations are well tolerated, as there is no severe or dose-limiting dermal irritation. All animals survive for the duration of the study and there are no test formulation-related clinical signs.

Systemic effects consist of decreased body weight gains and hematology, clinical chemistry and organ weight alterations at both doses of both formulations. Many of these changes are consistent with the pharmacologic activity of the test drug, a synthetic corticosteroid. Decreases in lymphocytes and thymus and spleen weights, relative to controls, are consistent with the immunosuppresive effects of the drug. Increases in cholesterol in both sexes, and serum triglycerides in females in all groups, appear to be associated with the glucocorticoid activity of this drug. Decreases in adrenal weights are a known effect of corticosteroids. Histopathological changes consist of deceased cellularity in the thymus, spleen, mesenteric, and mediastinal lymph nodes, as well as cortical atrophy in the adrenals, correlating with the macroscopic findings of small size. No remarkable differences between doses or betamethasone concentrations are noted. However, due to the differences in body weight of the treated animals in comparison to controls of approximately 10% or greater, resulting from decreased body weight gains, a "No Observed Adverse Effect Level" (NOAEL) cannot be established.

Example 17: Skin Permeation Testing

A skin permeation study is conducted using human skin, using the test procedure described below. Samples of Formulations C, F, G, and K (from Examples 2 and 3), and commercially available DIPROLENE lotion, are tested. Franz diffusion cells, with an average surface area of approximately 0.6 cm$^2$ and a volume of approximately 2 mL are used. Dermatomed human skin from three subjects is positioned between the donor and receiver compartments, such that for each test material there are three cells for each donor, for each of the 8 and 24 hours test durations. The integrity of the dermatomed human skin is measured by electrical impedance. The upper and lower donor chambers are filled with a PBS solution to allow for current conductance across the skin. The skin samples showing an impedance of <2000 ohms are discarded and replaced. Following measurement of skin impedance, the PBS solution is removed from the receiver compartment and replaced with 200 μL of 2% Brij® 98v in PBS. The side arm and donor chamber are then both covered with Parafilm™ prior to equilibrating in a water bath at 34-37° C. (to maintain a skin surface temperature of 32±10° C.) for at least 30 minutes prior to dosing. An additional Franz cell is also mounted but not dosed, and the temperature at the surface of the skin is continuously monitored using a temperature probe to ensure the skin surface temperature remains constant at 32±10° C. throughout the experiment. The cells are dosed with the test materials. After dosing, the upper donor chamber of the Franz cell is immediately replaced and secured. The Parafilm™ on the side arm is then removed and the receiver compartment is filled with pre-warmed receiver fluid. The Franz cell is then placed into a pre-calibrated water bath, which maintains a skin surface temperature of 32±10° C. The cells are left un-occluded for the duration of the experiment. At time=0, 200 μL of the receiver fluid is removed with a syringe prior to dosing, and fresh pre-warmed receiver fluid is used to replace the receiver fluid removed at this and each subsequent sampling time point. At the end of each test duration, diluent is employed to remove and quantify residual betamethasone dipropionate from the surface of the skin and donor chamber individually. The betamethasone dipropionate is extracted from the stratum corneum. The viable epidermal membrane and dermis layers of the skin are separated and the betamethasone dipropionate is extracted from both layers. Drug present in each layer is determined using HPLC.

Figure 2:
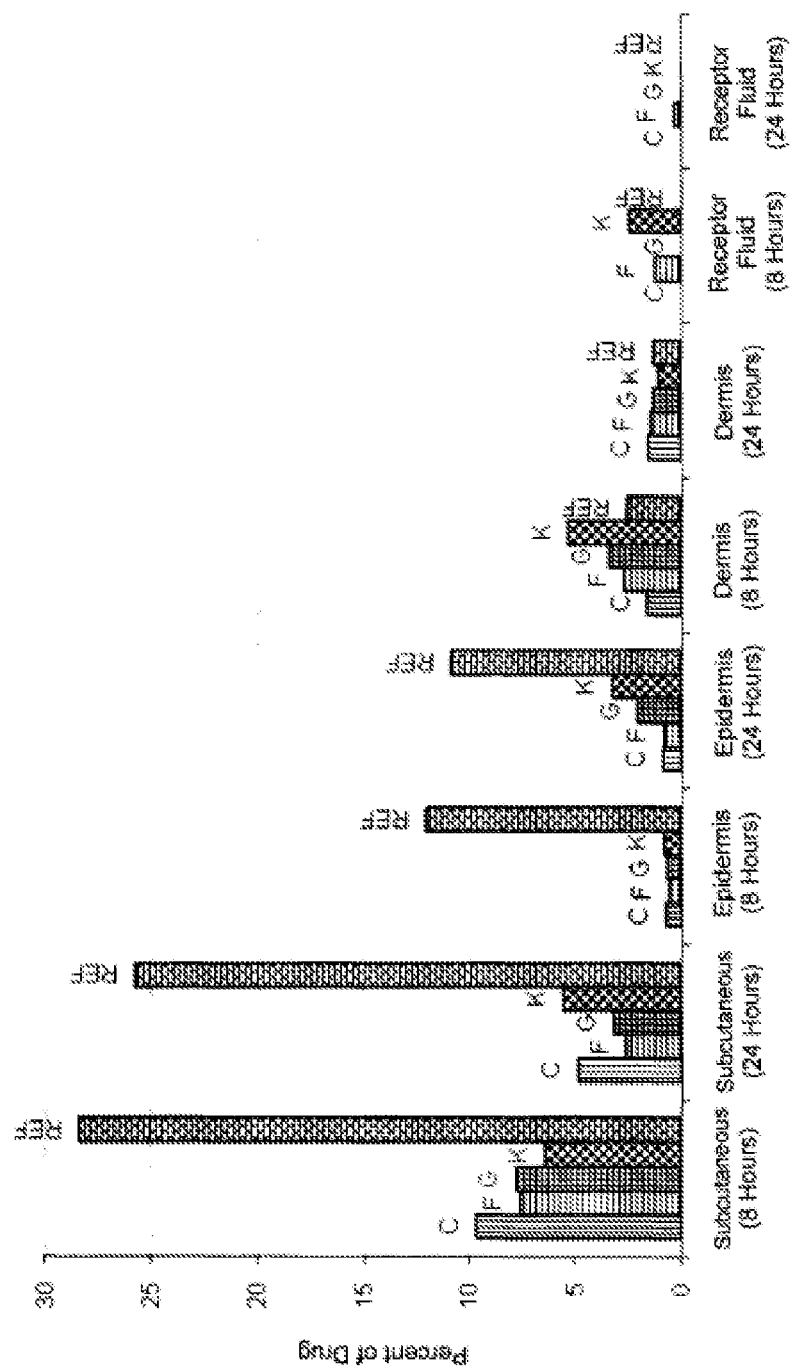
FIG. 2 shows the concentrations of drug in different skin layers at 8 hours and 24 hours after application, for certain formulations prepared in Examples 2 and 3.

Results of the skin permeation study are shown graphically in FIG. 2, where the "REF" bars are for DIPROLENE lotion. At 8 hours, the dermis drug levels are generally higher or equal for formulations of the examples, than levels for DIPROLENE lotion. Subcutaneous and epidermis levels are much lower for formulations of the examples than for DIPROLENE lotion. While it is not intended to be bound to any particular theory, the higher dermis levels can translate into higher efficacy, while lower epidermis levels can translate into lower skin atrophy potential for formulations of the examples than for DIPROLENE lotion. It is hypothesized that formulations of the examples allow the drug to penetrate skin more deeply, while the drug from DIPROLENE lotion penetrates mainly into the epidermis.

At 24 hours, the fall in dermis levels is steeper for formulations of the examples, when compared to DIPROLENE lotion. Steeper rates of fall can translate into lesser accumulation over multiple applications. Higher subcutaneous and epidermis levels for DIPROLENE lotion could be contributing to sustained dermis levels at 24 hours.

Dermis level variations may be due, to some extent, to formulation variables such as different polymers, drug concentrations, and the diethyleneglycol monoethyl ether ("DEGME") concentrations, and these variables are compiled in Table 6, where "HEC" is hydroxyethyl cellulose and "XG" is to xanthan gum.

TABLE 6

| Formulation | Betamethasone | DEGME | Polymer |
|---|---|---|---|
| C | 0.05% | 3% | HEC |
| F | 0.025% | 3% | HEC |
| G | 0.05% | 10% | HEC |
| K | 0.05% | 3% | XG |
| DIPROLENE | 0.05% | — | — |

What is claimed is:

1. A topical pharmaceutical composition comprising:
   clobetasol;
   an emulsifying agent;
   water;
   a water-immiscible substance; and
   a skin penetration enhancer selected from the group consisting of butanediol, polyethylene glycol monolaurate, diethylene glycol monoethyl ether, dimethylsulfoxide, decylmethylsulfoxide, lauric acid, oleic acid, valeric acid, isopropyl myristate, isopropyl palmitate, methyl propionate, ethyl oleate, and combinations thereof;
   wherein the composition is non-foaming, propylene glycol-free, alcohol-free, and propellant-free.

2. The composition according to claim 1, wherein the clobetasol is clobetasol propionate.

3. The composition according to claim 1, wherein the emulsifying agent comprises a cationic surfactant, anionic surfactant, zwitterionic surfactant, amphoteric surfactant, or any combination thereof.

4. The composition according to claim 3, wherein an emulsifying agent comprises a sorbitan fatty acid ester, a mixture of partial esters of sorbitol and its mono- and di-anhydrides with fatty acids, a polyethylene glycol stearate, a glycol stearate, sodium lauryl sulphate, cetyl trialkyl ammonium bromide, a polyoxyethylene sorbitan fatty acid ester, or any combination thereof.

5. The composition according to claim 1, wherein the water-immiscible substance comprises vegetable oil, saturated paraffin oil, mineral oil, fatty acid, fatty ester of a natural fatty acid, triglyceride of animal or vegetable origin, medium chain triglyceride, mixture of mono-, di- and/or tri-glycerides, wax, hydrogenated vegetable oil, and any combination thereof.

6. The composition according to claim 1, wherein the penetration enhancer is in amounts of about 0.001 percent to about 15 percent by weight.

7. The composition according to claim 6, wherein the skin penetration enhancer comprises a polyol or ester thereof, an ether, a sulfoxide, a fatty acid, a fatty acid ester, or any combinations thereof.

8. The composition of claim 1 further comprising an emollient comprising an oil of natural origin, a fatty acid or a monohydric alcohol ester thereof, a glycol, a branched aliphatic alcohol, or any combination thereof.

9. A method of treating a skin condition in a subject comprising topically administering an effective amount of a composition according to claim 1 to the subject;
   wherein the skin condition is one or more of atopic dermatitis, seborrheic dermatitis, eczema, plaque psoriasis, erythroderma psoriasis, and psoriasis of the scalp, steroid responsive dermatoses, erythema, or contact sensitivity reaction.

10. A propellant-free topical composition, comprising:
    clobetasol;
    an emulsifying agent from about 0.25% w/w to about 45% w/w of the composition;
    a skin penetration enhancer from about 0.001% w/w to about 15% w/w of the composition; and
    a water-immiscible substance;
    wherein the composition is non-foaming, propylene glycol-free and alcohol-free.

11. The composition according to claim 10, wherein the clobetasol is clobetasol propionate.

12. The composition according to claim 10, wherein the emulsifying agent comprises a cationic surfactant, anionic surfactant, zwitterionic surfactant, amphoteric surfactant, or any combination thereof.

13. The composition according to claim 12, wherein an emulsifying agent comprises a sorbitan fatty acid ester, a mixture of partial esters of sorbitol and its mono- and di-anhydrides with fatty acids, a polyethylene glycol stearate, a glycol stearate, sodium lauryl sulphate, cetyl trialkyl ammonium bromide, a polyoxyethylene sorbitan fatty acid ester, or any combination thereof.

14. The composition according to claim 10, wherein the water-immiscible substance comprises vegetable oil, saturated paraffin oil, mineral oil, fatty acid, fatty ester of a natural fatty acid, triglyceride of animal or vegetable origin, medium chain triglyceride, mixture of mono-, di- and/or tri-glycerides, wax, hydrogenated vegetable oil, and any combination thereof.

15. The composition according to claim 10, wherein the skin penetration enhancer comprises a polyol or ester thereof, an ether, a sulfoxide, a fatty acid, a fatty acid ester, or any combinations thereof.

16. The composition of claim 10 further comprising an emollient comprising an oil of natural origin, a fatty acid or a monohydric alcohol ester thereof, a glycol, a branched aliphatic alcohol, or any combination thereof.

17. A method of treating a skin condition in a subject comprising topically administering an effective amount of a composition according to claim 10 to the subject;
    wherein the skin condition is one or more of atopic dermatitis, seborrheic dermatitis, eczema, plaque psoriasis, erythroderma psoriasis, and psoriasis of the scalp, steroid responsive dermatoses, erythema, or contact sensitivity reaction.

* * * * *